United States Patent
Wada et al.

(10) Patent No.: US 6,379,884 B2
(45) Date of Patent: Apr. 30, 2002

(54) METHODS AND SYSTEMS FOR MONITORING INTRACELLULAR BINDING REACTIONS

(75) Inventors: H. Garrett Wada, Atherton; Javier A. Farinas, San Carlos; Theo T. Nikiforov, San Jose, all of CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/750,638

(22) Filed: Dec. 28, 2000

Related U.S. Application Data (60) Provisional application No. 60/174,976, filed on Jan. 6, 2000.

(51) Int. Cl.⁷ ................................................. C12Q 1/68
(52) U.S. Cl. .................. 435/4; 435/5; 435/6; 435/91.1; 435/91.2; 530/287.1; 530/387.1
(58) Field of Search ............. 435/4, 5, 6, 91.1, 435/91.2; 530/287.1, 387.1

(56) References Cited

U.S. PATENT DOCUMENTS

| | | |
|---|---|---|
| 4,269,511 A | 5/1981 | Erwin |
| 4,299,486 A | 11/1981 | Nogami et al. |
| 4,345,027 A | 8/1982 | Dolbeare |
| 4,390,403 A | 6/1983 | Batchelder |
| 4,745,285 A | 5/1988 | Recktenwald et al. |
| 5,057,413 A | 10/1991 | Terstappen et al. |
| 5,166,052 A | 11/1992 | Cercek et al. |
| 5,225,326 A | 7/1993 | Bresser et al. |
| 5,278,048 A | 1/1994 | Parce et al. |
| 5,302,349 A | 4/1994 | Dandiliker et al. |
| 5,304,487 A | 4/1994 | Wilding et al. |
| 5,395,503 A | 3/1995 | Parce et al. |
| 5,460,945 A | 10/1995 | Springer et al. |
| 5,496,697 A | 3/1996 | Parce et al. |
| 5,534,416 A | 7/1996 | Millard et al. |
| 5,626,134 A | 5/1997 | Zuckerman |
| 5,637,469 A | 6/1997 | Wilding et al. |
| 5,660,991 A | 8/1997 | Lakowicz et al. |
| 5,726,026 A | 3/1998 | Wilding et al. |

(List continued on next page.)

FOREIGN PATENT DOCUMENTS

| | | | |
|---|---|---|---|
| WO | WO9615576 | 5/1996 | |
| WO | WO9702357 | 1/1997 | |
| WO | WO9800231 | 1/1998 | |
| WO | WO9800705 | 1/1998 | |
| WO | WO9805959 | 2/1998 | |
| WO | WO9858074 | 12/1998 | |
| WO | WO9964840 | 12/1999 | |
| WO | WO-99/64840 | * 12/1999 | .......... G01N/15/06 |

OTHER PUBLICATIONS

Vives et al. (Journal of Biological Chemistry, vol. 272, No. 25, 1997, 16010–16017).*
Derossi et al. (Trends in Cell Biology, vol. 8, Feb. 1998, pp. 84–87).*

(List continued on next page.)

Primary Examiner—W. Gary Jones
Assistant Examiner—Janell E. Taylor
(74) Attorney, Agent, or Firm—Matthew B. Murphy (57) ABSTRACT

Intracellular binding reactions, and particularly DNA/DNA binding protein reactions are detected in situ, using intracellular fluorescence polarization detection. The methods comprise providing a biological cell having at least a first component of a binding reaction disposed therein. The cell is contacted with a second component of the binding reaction whereby the second component is internalized within the biological cell. At least one of the first and second components has a fluorescent label. The amount of binding between the first and second components within the cell is determined by measuring a level of polarized and/or depolarized fluorescence emitted from within the biological cell.

33 Claims, 5 Drawing Sheets

U.S. PATENT DOCUMENTS

| | | |
|---|---|---|
| 5,744,366 A | 4/1998 | Kricka et al. |
| 5,804,436 A | 9/1998 | Okun et al. |
| 5,804,448 A | 9/1998 | Wang et al. |
| 5,843,640 A | 12/1998 | Patterson et al. |
| 5,928,868 A | 7/1999 | Liu et al. |
| 5,942,443 A | 8/1999 | Parce et al. |
| 6,025,917 A | 2/2000 | Toyonaga et al. |
| 6,124,436 A * | 9/2000 | McClanahan et al. ... 530/387.1 |

OTHER PUBLICATIONS

Crino et al. (PNAS, vol. 95, pp. 2313–2318).*

Checovich et al. (Nature, vol. 375, May 1995, pp. 254256).*

Andersson, P.E. et al., "Biological Cell Assays on an Electrokinetic Microchip" *Transducers 97* 1997 International Conference on Solid–State Sensors and Actuators, Chicago (Jun. 16–19, 1997) pp. 1311–1314.

Bass, D.A. et al., "Flow Cytometric Studies of Oxidative Product Formation by Neutrophils: A Graded Response to Membrane Stimulation" *J. Immunol.* (1983) 130(4):1910–1917.

Brunk, K.D. et al., "Quantifying Folling Adhesion with a Cell–Free Assay: E–Selection an its Carbohydrate Ligands" *Biophysical Journal* (1997) 72–2820–2833.

Checkovich, W.J. et al., "Fluorescence polarization—a new tool for cell and molecular biology," *Nature* (1995) 375:254–256.

Crino, P. et al., "Presence and phosphorylation of transcription factors in developing dendrites," *Proc. Nat'l Acad. Sci., USA* (1998) 95:2313–2318.

Dandiliker, W.B. et al., "Fluorescence polarization in immunochemistry" *Immunochem.* (1970) 7:799–828.

DeRossi, D. et al., "Trojan peptides: the penetratin system for intracellular delivery" *Trends in Cell Biology* (1998) 8:84–87.

Kricka, L.J. *Ligand Binder Assays* (1985) New York: Marcel Dekker, Inc.

Lawrence, M.B. et al., "Neutrophils Roll on E–Selectin" *J. Immunology* (1993) 151(11):6338–6346.

Li, P.C.H. et al., "Transport, Manipulation, and Reaction of Biological Cells On–Chip Using Electrokinetic Effects" *Anal. Chem.* (1997) 69:1564–1568.

Lundblad, J.R. et al., "Fluorescence Polarization Analysis of Protein–DNA and Protein–Protein Interactions," *Mol. Endocrinology* (1996) 10(6):607–612.

Molecular Probes, *Handbook of Fluorescent Probes and Research Chemicals*, $6^{th}$ Edition (1996) pp. 32–33, 126–128, 219–225, 314–316, 377–398, 511, 552.

Molecular Probes, *Bioprobes 25* (1997) "Fluorescent Stains for Live Cells" (From the Internet).

Salimi–Moosavi, H. et al., "Biology Lab–on–a–chip for Drug Screening" *Solid State Sensor and Actuator Workshop* Hilton Head Island, South Carolina (Jun. 8–11, 1998) pp. 350–353.

Thomas, C.A. et al., "Fluorometric Assessments of Acrosomal Integrity and Viabilty in Cryopreserved Bovine Spermatozoa" *Biology of Reproduction* (1997) 56:991–998.

Vives, E. et al., "A Trancated HIV–1 Tat Protein Basic Domain Rapidly Translocates Through the Plasma Membrane and Accumulates in the Cell Nucleus," *J. Biol Chem.* (1997) 272(25):16010–16017.

* cited by examiner

METHODS AND SYSTEMS FOR MONITORING INTRACELLULAR BINDING REACTIONS

CROSS REFERENCE TO RELATED APPLICATION

This application claims the benefit of U.S. Provisional Application No. 60/174,976, filed Jan. 6, 2000, the disclosure of which is incorporated by reference herein in its entirety for all purposes.

BACKGROUND OF THE INVENTION

Many aspects of biological research rely upon the ability to perform extremely large numbers of chemical and biochemical assays. Increasing the throughput of screening assays has allowed researchers to adopt a more generalized approach to the overall screening process, as opposed to a more rational, predefined process. For example, in the pharmaceutical discovery process, large libraries of different compounds are generally screened against defined target systems to determine whether any of those compounds have a desired effect on that system. Once a compound is identified to have the desired effect, it is then subjected to more rigorous analysis.

Many high-throughput screening assay systems rely upon entirely in vitro models of biological systems. This is due, at least in part, to the ability to accurately control substantially all of the parameters of the model system that is being assayed to permit correlation from assay to assay, such as the quantity and purity of reagents, the environmental conditions of the assay, the operator performing the assay, and the like. Specifically, variation of any of these parameters can produce widely varying results in the performance of a given assay.

In many cases, these in vitro systems have proven to be effective models of the biochemical system of interest, and have led to the identification of promising pharmaceutical candidate compounds. However, in many instances it is desirable to use a model system that is a closer representation of what actually occurs in more complex systems, e.g., in vivo. Cell-based systems offer a closer model to these relevant biological systems, and have generally been widely adopted as screening assays. In particular, these cell based systems typically include a more complete range of biochemical events involved in a particular biological activity, where the overall biological activity or simply the outcome of that biological activity is of particular pharmacological interest. By way of example, when a cell surface receptor binds its ligand, it may activate a cell signaling pathway or cascade, where a protein, e.g., a DNA binding protein, is phosphorylated altering its activity and/or specificity. The binding of this protein to a particular nucleic acid sequence then results in an increase or a decrease in the level of expression of a particular gene product encoded by that nucleic acid sequence or the gene that comes under the control of that sequence. In looking for effectors of the activation of the gene, one could focus individually on each step in the pathway, and hopefully obtain a promising lead effector compound. Preferably, however, one screens the compound against the entire pathway, to thereby increase the chances of obtaining an effector of any one step in the pathway. This entire pathway screening is best carried out in whole cell systems.

It would generally be desirable to provide cell-based assays, and particularly cell based screening assays that are more reflective of complex biological systems. Further, it would be desirable to provide a simple assay format for monitoring the level of intracellular interactions, which interactions figure in a particular pathway of interest.

SUMMARY OF THE INVENTION

In a first aspect the present invention provides a method of detecting intracellular binding interactions. The method comprises providing a biological cell having at least a first component of a binding reaction disposed therein. The cell is contacted with a second component of the binding reaction whereby the second component is internalized within the biological cell. At least one of the first and second components has a fluorescent label. The amount of binding between the first and second components within the cell is determined by measuring a level of polarized and/or depolarized fluorescence emitted from within the biological cell. In preferred aspects, the methods measure and/or monitor the interaction between a protein and non-protein molecule, intracellularly.

Another aspect of the present invention is a method of monitoring activation of a cell signaling pathway. The method includes providing a cell which comprises a cell signaling pathway. At least one step in the cell signaling pathway comprises an intracellular binding interaction between a nucleic acid and a nucleic acid binding protein. The cell is contacted with a first nucleic acid whereby the first nucleic acid is internalized within the cell. The first nucleic acid comprises a fluorescent label and is capable of being bound by the nucleic acid binding protein. A level of binding between the nucleic acid binding protein and the first nucleic acid is monitored by monitoring a level of polarized and/or depolarized fluorescence emitted from within the cell. The amount of polarized and/or depolarized fluorescence is indicative of a level of activation of the cell signaling pathway.

A further aspect of the present invention is a method of screening for effectors of cellular function. The method comprises providing at least a first cell capable of at least one cellular function that is initiated by interaction of a nucleic acid sequence and a nucleic acid binding protein. A first nucleic acid having a fluorescent label is inserted into the cell wherein the first nucleic is capable of being bound by the nucleic acid binding protein. The cell is exposed to a test compound. An amount of binding between the first and second components within the cell is determined by measuring a level of polarized and/or depolarized fluorescence emitted from within the biological cell. An amount of binding between the first and second components within the cell is compared in the presence of the test compound to an amount of binding between the first and second components within the cell in the absence of the test compound.

DETAILED DESCRIPTION OF THE INVENTION

I. General Description

The present invention is generally directed to methods and systems for monitoring intracellular biochemical interactions, in situ, that are indicative of important cellular events. These methods are preferably applied in screening potential pharmaceutical compounds, also referred to as test compounds, in order to ascertain whether any such compounds have an effect on those interactions or upon the cellular events that lead to or result from such interactions. As noted above, a wide variety of specific intracellular binding or other associative biochemical interactions are integral steps in the biological pathways that lead to or result from important biological events, e.g., pharmacologically or medically relevant events. As a result, the ability to monitor those interactions in situ, as provided by the instant invention, is very useful.

As the present invention is directed to in situ analytical methods and systems, it typically requires the use of whole cell systems that comprise the elements of the particular binding or associative reaction of interest. Typically, in accordance with the invention, one of the components of the binding or associative reaction or interaction is already disposed within the whole cell system. By this is meant that at least one component of the binding interaction of interest is typically expressed by the cell, either natively, or as the result of genetic manipulation.

In accordance with the present invention, a second component of the binding reaction is inserted into the cell, e.g., from an exogenous source. The level of interaction between the two biochemical components is then ascertained. Depending upon the nature of the second component and the cell type used, the insertion of the second component may occur naturally, or it may require the addition of a translocation signal or functionality to the second component to facilitate the internalization of that component.

Typically, the interaction is monitored through the incorporation of detectable labels on at least one of the components whereby the binding event can be detected. In particularly preferred aspects, the second or exogenously introduced component has a relatively rotational correlation time, e.g., is relatively small compared to the size of the first component, and bears a fluorescent label group or moiety. In this case, the binding of the two components (the large endogenous component and small fluorescently labeled exogenous component) results in a change in the fluorescence anisotropy of the labeled component. This is readily detected by measuring the complex's ability to emit depolarized fluorescent light in response to polarized activation light. This change in the fluorescence anisotropy of the label is a result of the reduced rotational diffusion of the labeled component when bound to the other larger component.

In certain aspects, the relative level of interaction between the two components is monitored in the presence of one or more pharmaceutical test compounds, or under one or more particular environmental conditions. By monitoring the level of this interaction in the presence of test compounds, particular environmental conditions, or the like, one can ascertain the effects of such compounds or conditions on that interaction, or the biochemical events leading up to that interaction.

In particularly preferred aspects, the present invention provides methods, systems, kits and the like for monitoring the level of interaction between intracellular nucleic acid binding proteins and their target nucleic acid sequences, e.g., those to which the proteins bind. Many cellular functions are carried out through the initiation or reduction in the level of the transcription of certain genes, where the products of those genes carry out a specific cellular activity which is to be increased or decreased. A change in the level of transcription typically begins with the receipt of a signal by the cell indicating the need for a particular cellular function, e.g., the presence of a hormone, growth factor, or other signaling compound. The cell then initiates a signal cascade that results in the initiation or reduction in transcription of the gene and expression of the gene's product.

One of the primary ways that cells regulate the level of transcription of genes is through the use of transcriptional regulatory proteins that bind to sites on the cell's DNA proximal to the gene of interest to enhance or inhibit the transcription of that gene. Many of these transcriptional regulatory proteins are activated during the signal cascade, e.g., via phosphorylation of one or more residues on the protein, e.g., tyrosine, serine, and/or threonine, giving rise to their binding affinity to the regulatory sequence on the DNA strand. Alternatively, an inhibitory subunit can be phosphorylated, causing release of the active binding subunit. Thus, cellular events that are marked by changes in transcription levels are often preceded by the binding of these transcriptional regulatory proteins to the genetic material. As a result, monitoring the initiation of those cellular events can be accomplished by monitoring this binding interaction. As noted above, simply monitoring the binding reaction, in vitro, provides the investigator with substantially limited information as to the overall signaling process. Further, as these interactions typically occur within the cell, and in relatively short time-frames, observing the interactions can be quite difficult. Specifically, binding reactions between two or more interacting elements are generally assayed in cell extracts using a heterogeneous assay format. The present invention, however, utilizes a first component of the binding interaction, e.g., a DNA probe, and looks for changes in the optical properties of that component upon intracellular binding of the first component by another intracellular component. In particularly preferred aspects, the first component is fluorescently labeled and the optical property is the level of depolarized fluorescence that is emitted from the cell in response to a polarized excitation light source.

II. Cells

The methods and systems of the present invention are useful in virtually any type of biological cells, including, mammalian, bacterial, fungal, yeast, insect, and plant cells. In particularly preferred aspects, mammalian cells, e.g., CHO, HEK-293, L-cells, 3T3 cells, COS, THP-1 cells, blood cells, i.e., B cells, T cells, monocytes and neutrophils, etc., and bacterial cells are used. The specific cell type used typically varies depending upon the type of interaction that is sought to be monitored. For example, mammalian cells and specifically, human cells or animal cells transfected to express human proteins are typically preferred for screening potential human therapeutics, for their effects on mammalian and human systems, while other types of screening or experimentation may benefit from the use of other cell types, e.g., using bacterial or fungal cells to screen for potential antibiotic agents, etc.

Typically, well characterized cell lines that are predictive models of human cell functions are most preferred for their correlatability to human systems in pharmaceutical and medical research. Examples of preferred cell lines include, e.g., COS cells, CHO cells, HEK-293 cells, RBL-1, Jurkat, U937 and YB-1 cells.

The cells to be monitored may be provided in either immobilized form or as a suspension culture. For ease of processing, however, the cells are generally provided as a suspension of cells in an appropriate medium. In the case of these cell suspensions, cell density may vary depending upon the type of reaction vessel that is being employed, as well as the type of detection method that is being employed. Typically, determination of optimal cell densities is a matter of routine for one of ordinary skill in the art. In the case of flow-through embodiments of the invention, e.g., microfluidic systems, cell densities generally range from about 1 cell/nl to about 30 cells/nl in the reaction/detection portion of the vessel or channel. In the case of test tube or multiwell plate based reactions, cell densities typically range from about 1,000 cells/mm$^2$ to about 10,000 cells/mm$^2$. Of course, these ranges can also vary depending upon the cell types used, the relative adherence of the cells to the vessel surfaces as well as each other, and the like.

III. Binding Reaction

As noted previously, a wide variety of binding reactions are of particular interest to the biological research community, e.g., protein-protein interactions, receptor-ligand interactions, nucleic acid interactions, protein-nucleic acid interactions, and the like. In the intracellular environment, many of these reaction types are involved in the multiplicity of steps of signal transduction within cells. For example, activation of a particular cellular event is often triggered by the interaction between a cell surface receptor and its ligand. The signal from the receptor is often transmitted along via the binding of enzymes to other proteins, e.g., kinases, etc., which then pass the signal on through the cell until the ultimate desired response is achieved. Typically, the ultimate response is the increased or decreased expression of a particular gene product that is involved with the cellular event. This increase or decrease in expression is often the result of an increased or decreased level of interaction between the regulatory genetic sequence and newly activated gene regulating factors or proteins.

In accordance with the present invention, the binding interaction of interest occurs within the cell between at least first and second components of the interaction. The first component comprises a component of the particular interaction that is predisposed within the cell. By "predisposed" is meant that the first component exists within the cell prior to commencing the assay method. Typically, this refers to a component that is part of the cell, e.g., is expressed by the cell naturally, or as a result of introduction of an appropriate genetic construct within the cell. For example, where the first component comprises a receptor protein, a nucleic acid or nucleic acid binding protein, that component is typically expressed by the cell, either naturally or by virtue of an appropriate genetic construct introduced into the cell line.

In accordance with the present invention, the second component of the interaction of interest is typically provided, at least in part, as an exogenous probe that mimics the natural binding partner of the first component. Thus, the nature of the second binding component is dictated largely by the first binding component. For example, in the case of assays for intracellular protein-protein interactions, the second component comprises at least a polypeptide that includes the recognition structure or amino acid sequence that is necessary for binding by the first or cell associated component. In preferred aspects, monitoring of protein-protein interactions utilizes short peptide probes instead of the full-length exogenously introduced protein. For purposes of the instant invention, such peptide probes are considered non-protein molecules. These peptide probes may be recognized by virtue of their amino acid sequence, secondary structure, or modifications, e.g., phosphorylation in the case of kinase binding. Typically, such peptide probes will be between about 4 and about 100 residues in length, and more preferably, less than 50 residues in length, e.g., between about 4 and about 50. Typically, such peptides are less than about 10 kD, and more preferably, less than about 5 kD. Although useful in measuring protein/protein interactions, the present methods are particularly useful in measuring interactions between intracellular proteins and exogenously introduced non-protein molecules. Such molecules include, e.g., nucleic acids, carbohydrates, lipids, small molecules, i.e., binding fragments of full length proteins, including phosphorylated fragments, signaling molecules such as cAMP and cGMP, diacylglycerol (DAG), and the like.

Similarly, in the case of interactions between a particular DNA binding protein and a nucleic acid sequence, the second component typically comprises a nucleic acid probe, typically double stranded, that includes the appropriate recognition and binding sequence of nucleotides necessary for binding of the particular protein to the DNA strand. Typically, nucleic acid probes generally range from about 5 to about 100 bases in length. Typically, such probes range from about 10 to about 50 bases in length, so as to provide a sufficient binding sequence, without providing excessive sequence length that might impair measurement.

The second exogenous component typically includes one or more labeling groups in order to facilitate detection of the binding event. In preferred aspects, the label group on the exogenous second component of the interaction comprises a fluorescent group. A wide variety of fluorescent labels having a wide variety of excitation and emission maxima are known to those of ordinary skill in the art and are generally commercially available (e.g., from Molecular Probes, Eugene Oreg.). As noted previously, the fluorescent label group is used to monitor the binding event via a change in the level of polarized fluorescence resulting from binding of the first and second components, as is discussed in greater detail, below. In order to maximize the detectable shift in fluorescence polarization, it is generally desirable to provide for the greatest difference in rotational diffusion rates between the unbound labeled component and the labeled component when it is bound in a complex, e.g., with the second component. Typically, this is accomplished by providing the labeled component as a relatively small compound as compared to the unlabeled component. Specifically, the labeled component typically has a molecular weight that is equal to or less than that of the unlabeled component, and often, less than half, a fifth or even a tenth that of the unlabeled component. Thus, the labeled component will typically have a rotational diffusion rate that is at least twice that of the complex, preferably, at least 5 times that of the complex, and often, at least ten times that of the complex. Fluorescent polarization detection is described in greater detail, below.

While a single label group located on the exogenously introduced second component is preferred, in some cases, it may be desirable to provide both the first and second components with labeling groups to facilitate monitoring of the binding event.

As noted previously, in particularly preferred aspects, the present invention involves the monitoring of the interaction between a nucleic acid and an intracellular nucleic acid binding protein. In accordance with this aspect of the invention, the intracellular nucleic acid binding protein comprises a nucleic acid binding protein that is expressed by the cell. Typically, these binding proteins bind to specific nucleic acid sequences to regulate transcription of particular genes. These binding proteins are, in turn, activated by an upstream signaling event, e.g., tyrosine phosphorylation which, in turn, is in response to a particular environmental condition or other stimulus.

As described previously, an example of particularly interesting DNA/DNA binding protein interactions are those resulting from the signal transduction pathways of several classes of growth factors and cytokine receptors, that signal through extrinsic tyrosine kinases, e.g., the Janus kinases or "JAK", to activate genetic transcription regulation proteins, e.g., signal transcription activators of transcription or "STAT." Briefly, the STAT proteins, when phosphorylated at the appropriate residue(s), through a signal transduction event, dimerize. The dimerized STAT proteins have a greatly enhanced affinity for DNA sequences in the genome that enhance transcription of the downstream genes. Lamb et al., Drug Discovery Today, 3:122–130 (1998), Gouilleux et al., EMBO Journal 13(18):4361–4369 (1994).

The erythropoeitin (EPO) and interleukin-3 (IL-3) receptors, for example, when activated, in turn activate the JAK2 kinase which phosphorylates the STAT5 protein, which then binds to the PIE (Prolactin Inducible Element) and GAS (Gamma-Interferon Activated Site), to activate gene transcription (see, Lamb et al., supra).

By monitoring the level of binding of the STAT proteins, e.g., STAT5, to their target genetic regulatory sequences, e.g. PIE and GAS, one can monitor cytokine receptor activation, and screen for effectors of cytokine receptor activation in cells.

In operation, a fluorescently labeled, double stranded polynucleotide probe bearing the recognition/binding site for a particular regulatory genetic sequence, e.g., PIE or GAS, is introduced into the cells that are being observed. In the unbound state, these labeled probes will emit a particular level of depolarized fluorescence when excited with a polarized light source, due to their relatively fast rotational diffusion rate. When the appropriate receptor is activated, e.g., EPO or IL-3, the signaling cascade activates the appropriate binding protein, e.g., STAT5, which then binds to the binding and/or recognition sequence on the fluorescent probe. Once bound, the rotational diffusion rate of the fluorescent label, which is now part of the bound complex, is significantly slower, due to the larger molar volume of the complex. The slower rotational diffusion results in emission of more polarized (or less depolarized) fluorescence from the bound probe as compared to the free probe. This shift in the level of fluorescence polarization is then detected, providing a detectable event that corresponds with receptor activation. The detection of this binding interaction provides a direct reporter signal for activation of a the signal transduction pathway, e.g., receptor activation.

In many cases, e.g., where the second component comprises a nucleic acid compound, it may be necessary to incorporate a translocation functionality on the second component in order to facilitate the translocation or internalization of that component from the outside to inside the cell. As used herein, the term "translocation functionality" refers to a chemical compound, group or moiety that increases the cell's ability to internalize another compound or material. Examples of such translocation functionalities include peptide recognition/transport sequences, liposomal compositions, or the like. Alternative translocation methods and compositions are also utilized in accordance with the present invention to induce uptake of the second component, including, e.g., electroporation, cell permeating compositions containing, e.g. PEG, porins, saponins, streptolysin or the like.

In particularly preferred aspects, and particularly those aspects where the second component is a nucleic acid material, the translocation functionality comprises a polypeptide sequence that increases the internalization of the second component. Examples of particularly preferred peptide sequences include trojan peptides. See Derossi et al., Trends in Cell Biol. 8(2):84–87 (1998), incorporated herein by reference in its entirety for all purposes. In particular, a labeled nucleic acid probe is coupled to a relatively short polypeptide that facilitates the translocation of the nucleic acid probe into the cell where the assayed binding reaction occurs. Examples of preferred polypeptides include those derived from homeodomain proteins, which generally belong to a class of transcription factors involved in multiple morphological processes, e.g., derived from whole or fragments of ANTENNAPEDIA homeodomain (Antp-HD), a Drosophila transcription factor, i.e., amino acids 43–58 (Allinquant et al., J. Cell Biol. 128:919–927 (1995). Similarly, polypeptides derived from residues 48–60 of the HIV-1 tat protein, e.g., having sequences homologous to this sequence C(Acm)GRKKRRQRRRPPQC (SEQ ID NO:1) (C(Acm)=cysacetamidomethyl), are also preferred for use as translocation functionalities (Vives et al., J. Biol. Chem. 272:16010–16017 (1997)).

IV. Fluorescence Polarization Detection

In preferred aspects, as noted above, monitoring of the interaction event of interest is accomplished through fluorescence polarization detection. In particular, fluorescence polarization detection provides a relatively simple, homogeneous detection method for binding interactions. Measurement of differential polarization of free and bound ligands has long been utilized to determine relative ligand binding levels, and even to screen for compounds or conditions that might affect that binding. To date, such assays have been carried out in a contained fluid system, e.g., a cuvette or multiwell plate, where fluid components of the binding reaction, e.g., a labeled ligand and its receptor, are mixed in the presence or absence of a compound to be tested. Surprisingly, in accordance with the present invention, fluorescence polarization also provides a useful measurement tool for detecting intracellular binding reactions.

The principles behind the use of fluorescence polarization measurements as a method of measuring binding among different molecules are relatively straight-forward. Briefly, when a fluorescent molecule is excited with a polarized light source, the molecule will emit fluorescent light in a fixed plane, e.g., the emitted light is also polarized, provided that the molecule is fixed in space. However, because the molecule is typically rotating and tumbling in space, the plane in which the fluoresced light is emitted varies with the rotation of the molecule. Restated, the emitted fluorescence is generally depolarized. The faster the molecule rotates in solution, the more depolarized it is. Conversely, the slower the molecule rotates in solution, the less depolarized, or the more polarized it is. The relationship between the polarization value (P) for a given molecule and the molecule's "rotational diffusion rate" or "rotational correlation time," (sometimes termed the "rotational relaxation time") or the amount of time it takes the molecule to rotate through an angle of 57.3° (1 radian), is given by the Perrin Equation:

$$\frac{1}{P} - \frac{1}{3} = \left(\frac{1}{P_0} - \frac{1}{3}\right)\left(1 + \frac{T_F}{T_C}\right)$$

where $P_0$ is the limiting polarization value, $T_F$ is the fluorescent lifetime of the fluorescent label and $T_C$ is the rotational correlation time. The smaller the rotational correlation time, the faster the molecule rotates, and the less polarization will be observed, e.g., the more depolarized the fluorescent emissions. The larger the rotational correlation time, the slower the molecule rotates, and the more polarization will be observed, e.g., the less depolarized the emitted fluorescence will be. Rotational correlation time is related to viscosity ($\eta$), absolute temperature (T), molar volume (V), and the gas constants (R). The rotational correlation time is generally calculated according to the following formula:

Rotational Correlation Time=$3\eta V/RT$

As can be seen from the above equation, if temperature and viscosity are maintained constant, then the rotational correlation time, and therefore, the polarization value, is directly related to the molecular volume. Accordingly, the larger the molecule, the higher its fluorescent polarization value, and conversely, the smaller the molecule, the smaller its fluorescent polarization value. Typically, the binding partners for a given assay are chosen such that $T_F > T_C$ when the binding partners are not bound and $T_F < T_C$ when they are bound.

In the performance of fluorescent binding assays, a typically small, fluorescently labeled molecule, e.g., a ligand, antigen, oligonucleotide or nucleic acid probe, etc., having a relatively fast rotational correlation time, is used to bind to a much larger molecule, e.g., a receptor protein, antibody, complementary nucleic acid target sequence etc., which has a much slower rotational correlation time either on its own or as a part of the complex. The binding of the small labeled molecule to the larger molecule or in the larger complex significantly increases the rotational correlation time (decreases the amount of rotation) of the labeled species, namely the labeled complex over that of the free unbound labeled molecule. This has a corresponding effect on the level of polarization that is detectable. Specifically, the labeled complex presents much higher fluorescence polarization than the unbound, labeled molecule. The polarization value can then be used to determine the level of bound and free fluorescent compound.

Generally, the fluorescence polarization level is calculated using the following formula:

$P = [I(\|) - I(\perp)] / [I(\|) + I(\perp)]$

Where $I(\|)$ is the fluorescence detected in the plane parallel to the excitation light (also termed "polarized fluorescence"), and $I(\perp)$ is the fluorescence detected in the plane perpendicular to the excitation light (also termed "depolarized fluorescence"). Thus, as can be seen from this equation, the polarization value P is related to the ratio of polarized to depolarized fluorescence.

In performing screening assays, e.g., for potential inhibitors, enhancers, agonists or antagonists of the binding function in question, the change in fluorescence polarization of bound versus free labeled ligand is compared in the presence and absence of different compounds, to determine whether these different compounds have any effect on the binding function of interest. In particular, in the presence of inhibitors of the binding function, the fluorescence polarization will decrease, as more free, labeled ligand is present in the assay. Conversely, enhancers of the binding function will result in an increase in the fluorescent polarization, as more complex and less free labeled ligand are present in the assay.

V. Applications

The methods and systems of the present invention generally have a variety of uses in the research and diagnostic fields.

A. Expression Monitoring

The most notable uses for monitoring intracellular binding reactions in accordance with the methods and systems of the present invention is in monitoring gene expression in response to a particular stimulation or activation event, e.g., receptor activation via ligand binding, or the like.

In general, a cell's response to a given stimulus can be coupled to the increased or decreased expression of certain gene products. This may take the form of natural expression of gene products or engineered expression. In the case of engineered expression, this can be done by engineering indicator cell lines that have stimulus responsive regulatory elements controlling gene products, such as reporter genes. Expression is then monitored by detecting expression of the reporter gene product, typically an enzyme (e.g., $\beta$-galactosidase, luciferase, alkaline phosphatase, etc.) that produces an easily detectable product, such as a colored, chemiluminescent or fluorescent product. In the past, this has been accomplished by attempting to stimulate the cells, lyse the cells and look for increased levels of RNA resulting from increased expression, which requires several hours for gene transcription and a large number of complex steps, e.g., cell lysis and purification, amplification of nucleic acids, labeling, and the like. Both of these methods are performed after the fact as opposed to in real time.

As noted above, changes in expression levels of genes are typically preceded by increased or decreased interaction of that gene's regulatory region with DNA binding, gene regulation proteins. These changes in binding interactions are rapid, typically occurring within 60 seconds of stimulation, and are directly monitored using the above-described methods.

B. Screening Applications

While the methods and systems of the present invention have a variety of uses in research and diagnostic applications, as noted previously, they are most preferably applied in screening applications, and particularly pharmaceutical screening applications. In particular, when determining whether a particular compound has useful pharmacological activity, it is generally desired to screen the compound against a biochemical system model, in vitro, where interaction of the components of the biochemical system is mimetic of the interaction of components of an actual in vivo system in which a particular pharmacological activity would be desirable, e.g., inhibition of undesired reactions or occurrences or enhancement of desired reactions. The components of the biochemical system are exposed to the particular compound and their level of interaction is ascertained and compared to a negative or positive control, e.g., where no compound or a compound having a known effect is present, respectively.

The assay methods and systems are generally parallelized, e.g., carried out in parallel, in order to increase the number of different test compounds that may be screened at a given time. In conventional laboratories, this is carried out by depositing all of the assay reagents into separate wells in multi-well microplates, e.g., 96, 384 or 1536 well plates. A different test compound or control is then introduced into each of the various different wells, and the effects of each of the test compounds on the biochemical system of interest are then determined, e.g., using a multi-well plate reader to detect the optical signals associated with the screening assay, e.g., fluorescence polarization shifts.

Using these methods, one can rapidly screen large numbers or libraries of different test compounds for potential pharmacological activity. Typically, libraries of test compounds are derived from any of a variety of known origins, including isolation from natural sources, combinatorial chemistry methods, or the like. As such, these test compounds may include isolated small molecule organic or inorganic compounds, as well as isolates or mixtures of materials from plant, animal, fungal or bacterial extracts, or the like. While traditional laboratory vessels are easily employed in the methods and systems of the invention, as described below, continuous flow methods and systems, and particularly those employing microfluidic channel networks and systems, as described in greater detail, below.

The methods and systems of the invention are particularly useful in performing such screening assays. In particular, these assay methods and systems are used to screen libraries of potential pharmaceutical compounds or the like for an effect on the intracellular binding reaction of interest, or on events that precede and lead to those intracellular binding reactions, e.g., receptor activation.

In performing these screening assays, a cell is initially provided that includes at least a first component of the binding interaction of interest, e.g., a particular DNA binding protein. The second component of the binding interaction, e.g., a labeled nucleic acid probe, is then introduced into the cell to permit it to be bound by the first component. Either during or subsequent to the introduction of the second component into the cell, the cell is contacted with a test compound that is being screened. The cell is also exposed to any compounds or conditions required to activate the signaling cascade reaction that results in the binding reaction of interest, e.g., a ligand for a particular receptor, e.g., cytokines, etc.

The relative level of binding of the first and second components, e.g., as determined by comparing fluorescence polarization of activated cells to that of non-activated cells, is then ascertained. An increase or decrease in binding in the presence of the test compound is indicative of a change in the level of signal transduction events leading up to and including the binding reaction. The precise effect of the test compound on the overall signal transduction, e.g., whether it enhances or inhibits the pathway will depend upon the nature of the signal pathway, e.g., whether activation of the pathway is a negative or positive regulatory event. For example, in many cases, pathway activation results in increased binding of the first and second components, e.g., DNA binding proteins and regulatory gene sequences. In those cases, exposure of the cell to enhancers of pathway activation will show a further relative increase in the level of binding. Conversely, where a pathway results in reduced binding of two components, an enhancer of the signal pathway would lead to a decrease in the binding level.

VI. Assay Systems

A. Generally

A variety of systems may be used in carrying out the assay methods described above. These include conventional assay systems that rely upon the use of multi-well plates and plate reader detection systems available from, e.g., Life Technologies, Molecular Devices Inc., and LJL Biosystems, as well as more advanced systems, such as microfluidic or array based technologies.

Figure 1:
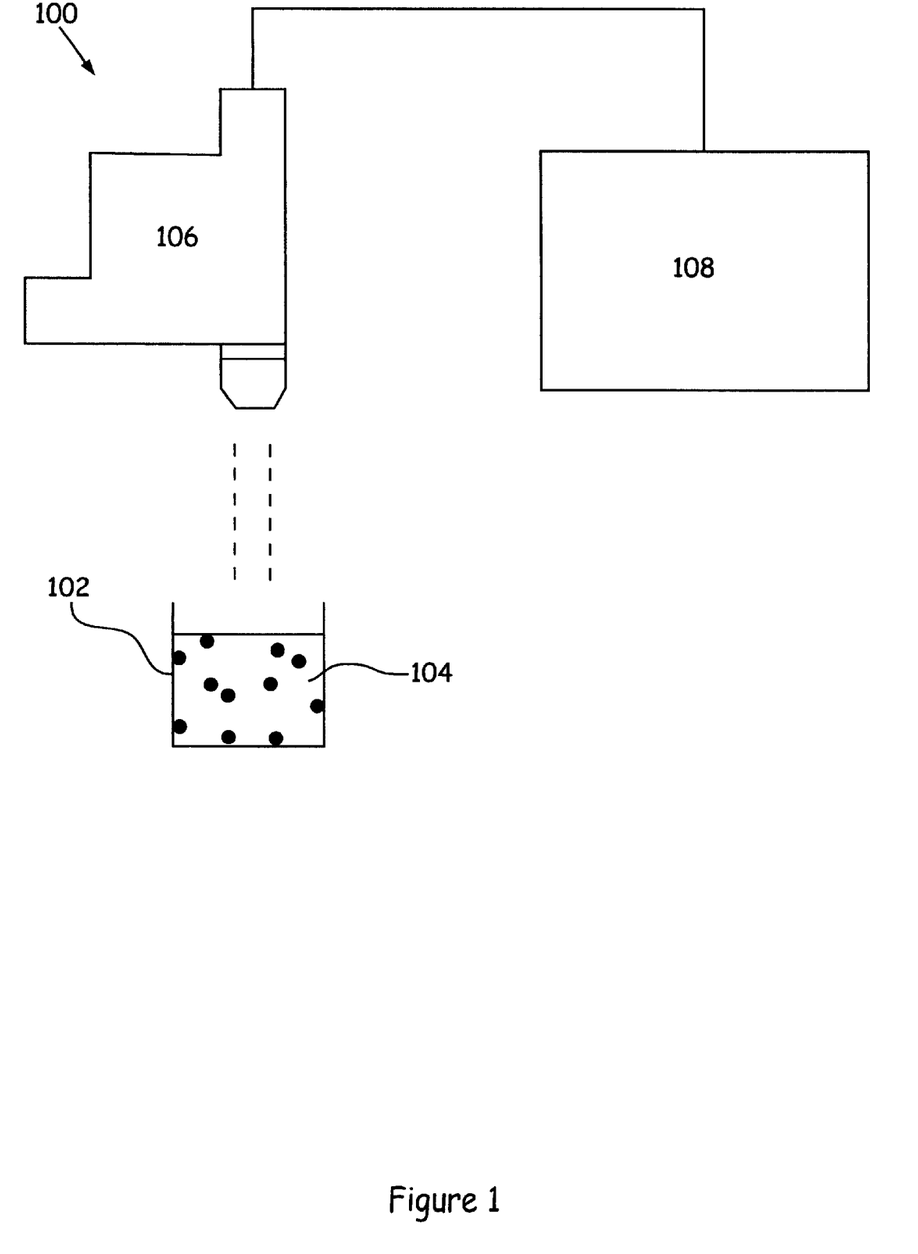
FIG. 1 schematically illustrates a system for carrying out the assay methods of the present invention.

A general schematic of a system for carrying out the methods of the invention is illustrated in FIG. 1. As shown, the system 100 includes a reaction vessel 102, in which the assay reaction is carried out. The reaction vessel includes a cell suspension 104 disposed therein. The reaction vessel 102 optionally includes a conventional assay vessel, such as a test tube, or a well of a multiwell plate, e.g., a 96, 384 or 1536 well plate. Alternatively, the reaction vessel 102 comprises a flow through conduit, such as a capillary channel or a channel in a microfluidic channel network, as described below.

A detector or detection system 106 is typically disposed within sensory communication of the contents of the reaction vessel. The phrase "within sensory communication" generally refers to the detector that is positioned relative to the reaction vessel 102 so as to be able to receive a particular signal from that receptacle. In the case of optical detectors, e.g., fluorescence or fluorescence polarization detectors, sensory communication typically means that the detector is disposed sufficiently proximal to the receptacle that optical, e.g., fluorescent signals are transmitted to the detector for adequate detection of those signals. Typically this employs a lens, optical train and/or other detection elements, e.g., a CCD, that is focused upon a relevant transparent or open portion of the receptacle to efficiently gather and record these optical signals. In the case of thermal or electrochemical signals, sensory communication requires actual contact between portions of the detector and the contents of the vessel, e.g., through thermal probes, electrodes, or the like.

The detector 106 is typically operably coupled to a computer 108 for receipt and processing of the signals received by the detector. Optionally, in the case of microfluidic systems, the computer also functions to control movement of material through the channels of the device, e.g., by instructing a fluid controller (not shown), as well as sampling activities for bringing test compounds or other reagents into the channels of the device. As described with reference to FIG. 3, below.

B. Microfluidics

As noted above, in preferred aspects, the assay systems of the invention utilize microfluidic channels and/or channel networks as the reaction vessels. These microfluidic systems provide for increased throughput, reduced reagent consumption, improved integration and automation over conventional systems, e.g., tube or well based systems. Microfluidic screening assay methods and systems have been described previously. See, e.g., U.S. Pat. No. 5,942,443. Similarly, use of fluorescence polarization detection in flowing microfluidic systems has been described in, e.g., Published International Patent Application No. PCT US99/12671, as have cell based assay methods and systems, see, e.g., Published International Patent Application No. PCT US99/13918. Each of the above references is incorporated herein by reference in its entirety for all purposes.

As used herein, the term "microfluidic" generally refers to one or more fluid passages, chambers or conduits which have at least one internal cross-sectional dimension, e.g., depth, width, length, diameter, etc., that is less than 500 $\mu$m, and typically between about 0.1 $\mu$m and about 500 $\mu$m. In the devices of the present invention, the microscale channels or chambers preferably have at least one cross-sectional dimension between about 0.1 $\mu$m and 200 $\mu$m, more preferably between about 0.1 $\mu$m and 100 $\mu$m, and often between about 0.1 $\mu$m and 20 $\mu$m. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

The body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device. In particular, these microfluidic devices are typically fabricated from two or more planar solid substrates. A series of interconnected grooves is generally fabricated into the surface of the first of the two substrates. The second substrate is then overlaid and bonded to the surface of the first substrate to seal the grooves and define the integrated fluidic channels of the device. Typically one of the substrates includes one or more ports, e.g., holes, disposed through the substrate, that are positioned such that the holes are in fluid communication with the integrated channels in the complete assembled device. These holes then function as reservoirs for fluid introduction into the channels of the device, as well as providing electrical access points for the various channels for use in, e.g., controlled electrokinetic material transport systems.

Figure 2A:
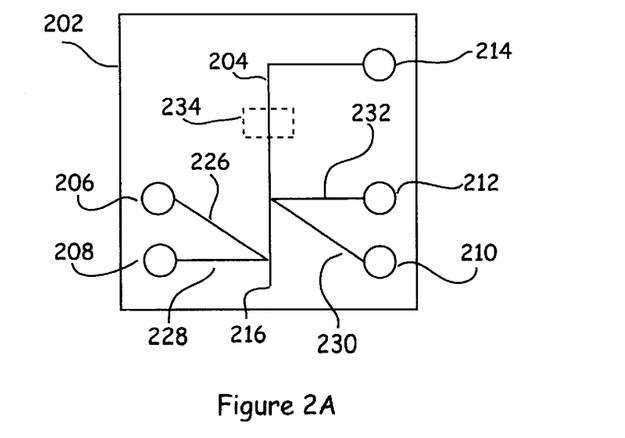
FIG. 2 schematically illustrates a microfluidic device for use in carrying out the assay methods of the present invention.
Figure 2B:
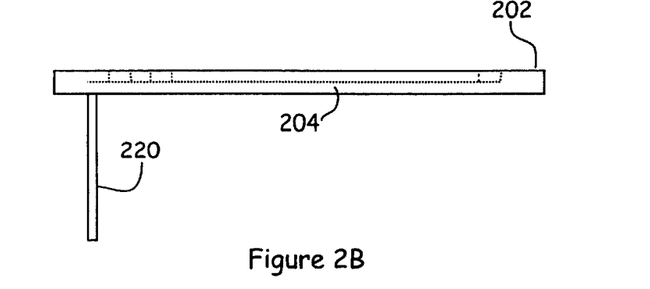
Figure 2C:
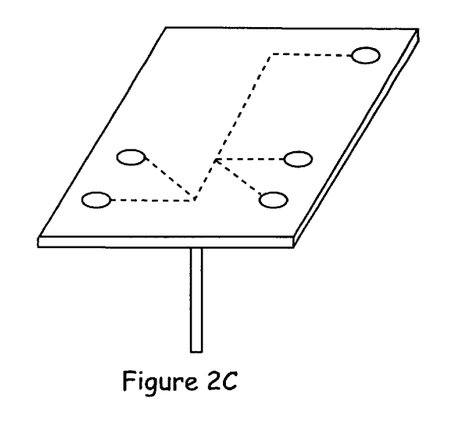

One example of a microfluidic device useful in carrying out the assays described herein is illustrated in FIG. 2. As shown, the device 200 includes a body 202 having a main analysis channel 204 disposed within its interior. At one terminus, main channel 204 is in fluid communication with waste reservoir 214. At the other terminus, main channel 204 is in fluid communication with an external sampling capillary or pipettor 220, via channel junction 216. Specifically, external capillary 220 is attached to the body 202 of the device 200, such that the channel within the capillary is fluidly connected to the main channel 204. Additional channels 226, 228, 230 and 232 intersect the main channel 204 and connect the main channel to reservoirs 206, 208, 210 and 212, respectively. These reservoirs 206–212 are used to introduce reagents into the main channel, including cell suspensions, assay reagents, buffers, and the like. In operation, the cell suspension and second component of the binding reaction, e.g., a nucleic acid probe, are flowed into the main channel 204 from, e.g., reservoirs 208 and 210. Appropriate diluents are also optionally added from reservoirs 206 and 212. As shown, fluid transport is driven by application of a vacuum source, e.g., to reservoir 214. Periodically, plugs of fluid containing test compounds are introduced into main channel 204 from capillary 220, e.g., by placing the open end of capillary 220 into a source of the test compound and drawing a volume of the test compound into the capillary channel and then up into the main channel 204. The results of the assay are then detected at a point in the main channel, e.g., detection window 234, e.g., by a fluorescence polarization detector.

Figure 3:
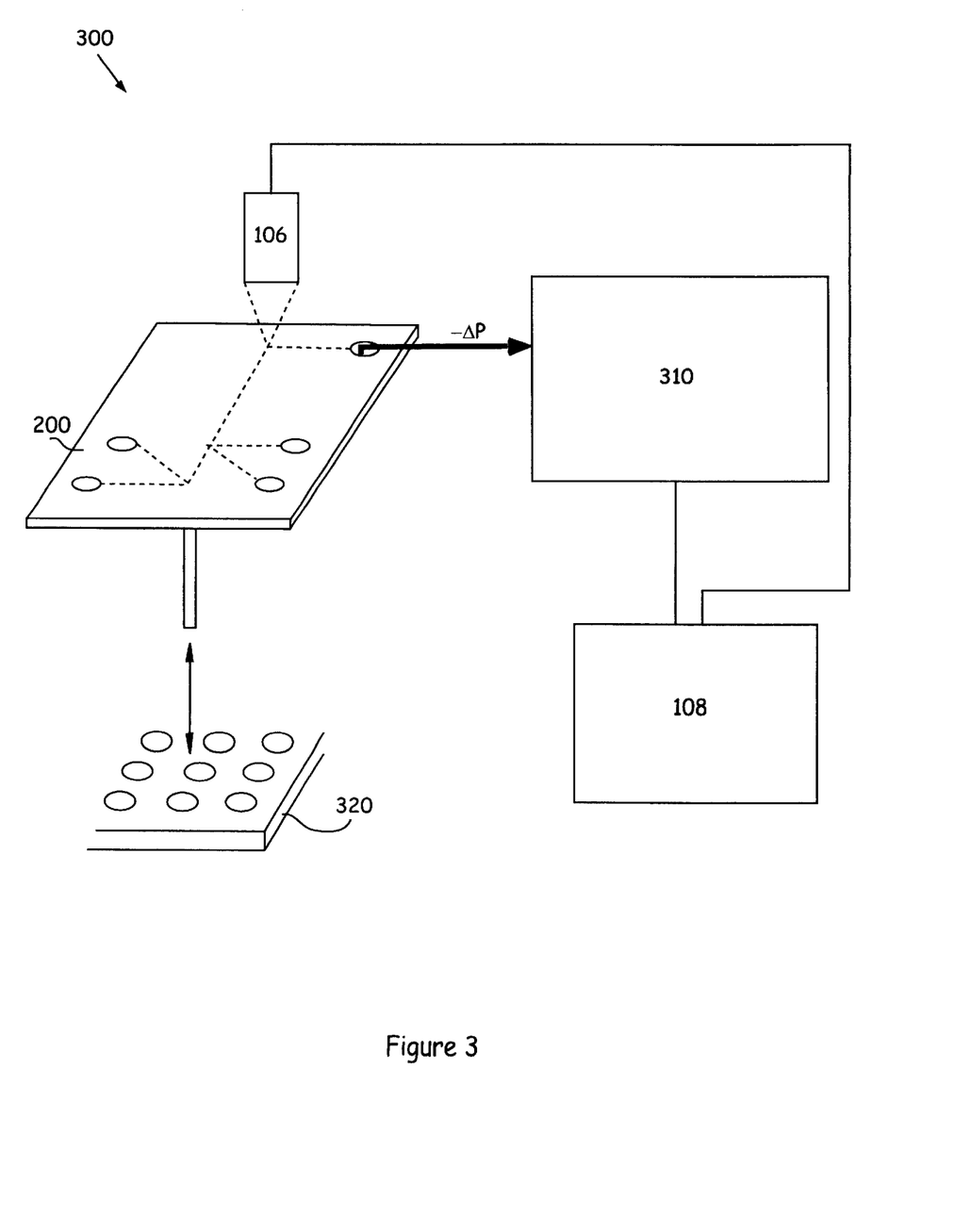
FIG. 3 schematically illustrates a system incorporating a microfluidic device for carrying out the assay methods of the present invention.

FIG. 3 schematically illustrates a microfluidic device 200 incorporated in an overall system. As shown, and with reference to FIGS. 1 and 2, the system includes device 200. A detector 106 is positioned to be within sensory communication with main channel 104. The device 200 is also operably connected to a flow controller 310 which directs fluid movement through the channels of the device 200. As shown, the flow controller 310 comprises a vacuum controller that applies a negative pressure to at least one of the wells of the device 200 (as indicated by the black arrow). Other methods of flow control are also optionally used in the systems described herein, including, e.g., pressure control at multiple reservoirs, and electrokinetic control via electrodes in contact with fluid in the various reservoirs of the device. Controlled electrokinetic transport of materials in microfluidic channel systems and use of such microfluidic systems in performing screening assays is described in detail in U.S. Pat. Nos. 5,779,868, 5,858,195, 5,976,336, and 5,942,443.

The system also includes a computer 108 that is operably coupled to the detector 106, for recording, storing and optionally analyzing the data from the detector 106. The computer is optionally operably coupled to the flow controller 310, as well. As such, the computer can also instruct the operation of the flow controller in accordance with user input and/or preprogrammed instructions, in order to provide desired fluid flow characteristics, e.g., rate, direction etc., through the channels of the device. As used herein, the term "operably coupled" refers to a connection between two component wherein one component is capable of communicating with the other. Operable coupling includes but is not limited to electrical, hydraulic, pneumatic, mechanical, optical and radio communication.

C. Detection Instrumentation

As noted previously, in preferred aspects, fluorescence polarization is used to detect intracellular binding events in the methods of the present invention. As such, specialized detection systems are typically incorporated into the systems of the invention. Specifically, such systems typically include a source of polarized excitation light that is directed at a given sample material, e.g., through an appropriate optical train. Fluorescence emitted from the sample is then collected, e.g., by the same optical train, and split into fluorescence that is in the same plane as the excitation light and fluorescence that is in the perpendicular plane. The amount of fluorescence in each plane is then detected.

Figure 4:
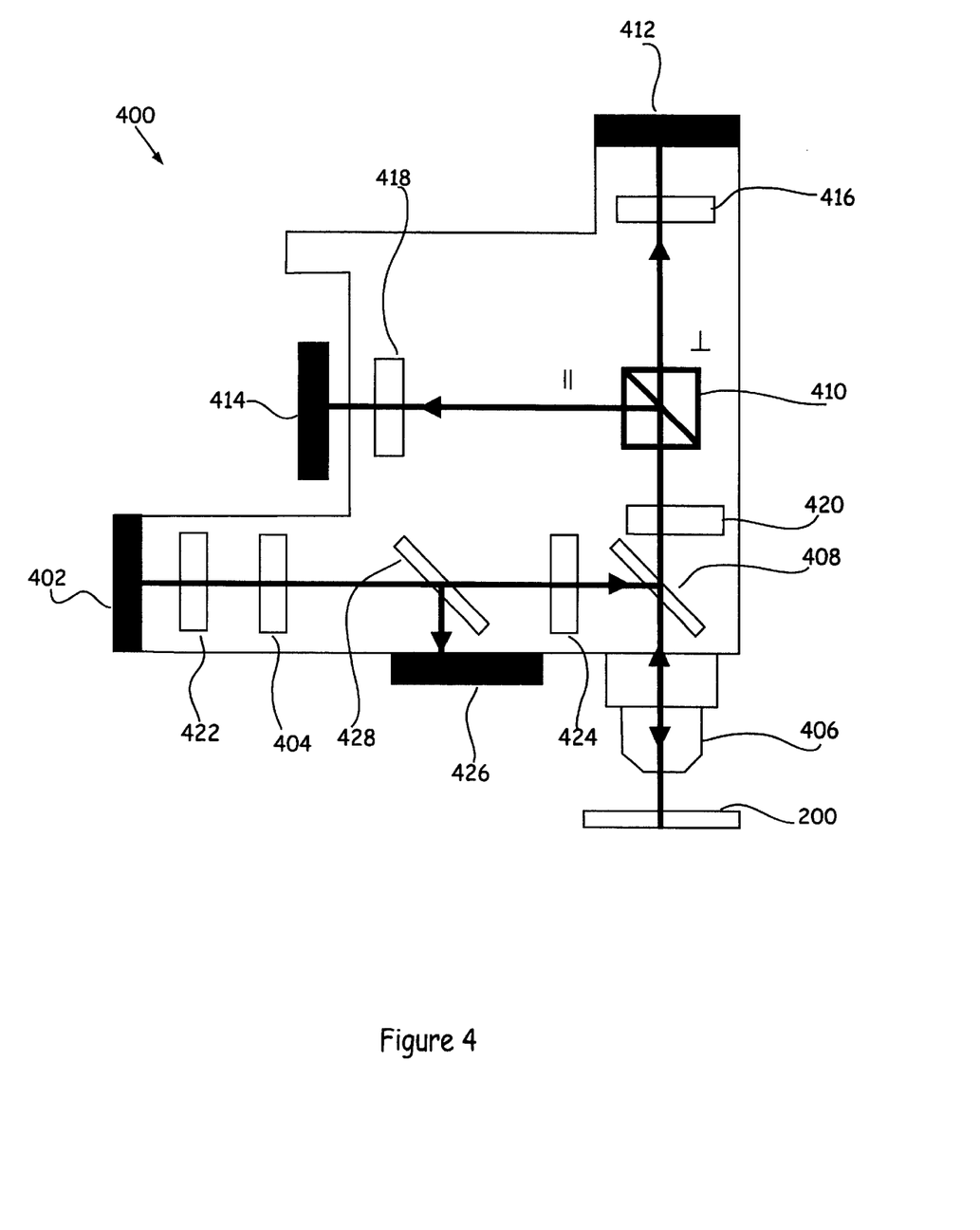
FIG. 4 schematically illustrates a modular detector for performing fluorescence polarization detection in accordance with certain aspects of the present invention.

An example of an optical detection system for use in fluorescence polarization detection is illustrated in FIG. 4. As shown, the fluorescence polarization detector 400 includes a light source 402, which generates light at an appropriate excitation wavelength for the fluorescent compounds that are present in the assay system. Typically, coherent light sources, such as lasers, laser diodes, and the like are preferred because of the highly polarized nature of the light produced therefrom. The excitation light is optionally directed through a polarizing filter 404, which passes only light in one plane, e.g., polarized light. The polarized excitation light is then directed through an optical train, e.g., including microscope objective 406, which focuses the polarized light onto the channel in the microfluidic device 200, through which the sample to be assayed is flowing, to excite the fluorescent label present in the sample.

Fluorescence emitted from the sample is then collected, e.g., through objective 406, and passed through the optical train including e.g., a dichroic beamsplitter 408 for separating fluorescence from reflected excitation light, polarizing beam splitter 410 for separating the emitted fluorescence into a component that is in the plane parallel to the excitation light, and the plane perpendicular to the excitation light. The separated polarized light components are then separately directed to separate detectors 412 and 414, respectively (as indicated by the symbols $\parallel$ for parallel fluorescence and $\perp$ for perpendicular fluorescence), where each component is quantified. Photomultiplier tubes (PMTs) are generally preferred as light detectors for the quantification of the light levels, but other light detectors are optionally used, such as photodiodes, CCDs, or the like. Additional optical elements are also optionally included, i.e., detector focusing lenses 416 and 418, emission filter 420, laser line filter 422, laser collimation lens 424, as well as a reference detector 426 and accompanying beamsplitter 428.

As described above, the detector is typically coupled to a computer or other processor, which receives the data from the light detectors, and includes appropriate programming to compare the values from each detector to determine the amount of polarization from the sample, e.g., in accordance with the processes and equations set forth herein. The computer also typically displays the polarization data in an appropriate graphical format that is convenient for the user

VII. Kits

The present invention also provides kits for the use in practicing the above-described methods. Typically, such kits optionally include cells or cell suspensions that include at least a first component of a binding reaction disposed within their interior portions, e.g., endogenous DNA binding proteins, etc. Alternatively, the investigator may use cells of their own selection as needed for the desired assay. The kits also typically include at least a second component of the binding reaction as a separate reagent, e.g., a fluorescently labeled nucleic acid probe, that is capable of being taken into the cells and bound by the first component. The kits optionally include such reagents as well as additional reagents in liquid or lyophilized forms, such as buffers, detergents, salts or other elements useful in carrying out the assay, where all components of the kit are disposed in a common package. In certain aspects, the kits also include the assay or reaction receptacle, which is optionally a test tube, multiwell plate or microfluidic device. In addition, such kits typically include appropriate instructions for carrying out the methods described above.

EXAMPLES

Figure 5:
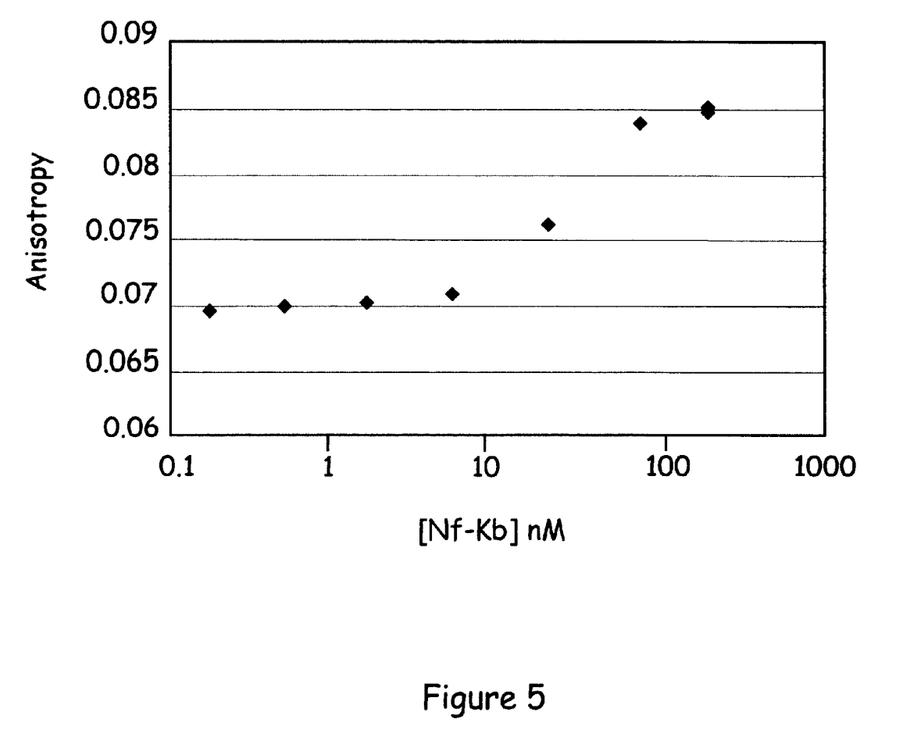
FIG. 5 illustrates detection of binding of DNA binding proteins to a labeled nucleic acid probe by a shift in fluorescence polarization levels.

A 17 bp, fluorescein labeled double stranded DNA probe was mixed with serial dilutions of recombinant p50 fragment of NF-Kb DNA binding protein in binding buffer containing 12 mM HEPES, 4 mM Tris, 60 mM KCl, 0.4 mM EDTA, 10% glycerol, 2 mM DTT and poly-dAdT, and each was incubated for 45 minutes at room temperature. The each of the different dilutions were then flowed through a microscale capillary channel and monitored using a fluorescence polarization detector as shown in FIG. 4. As can be seen, increased concentration of binding protein, which leads to increased levels of binding, also leads to an increase in the level of fluorescence polarization, showing that fluorescence polarization is a useful method of detecting these interactions.

When the Antp-HD peptide is coupled to the 17 bp fluorescein labeled ds-DNA probe, cells expressing NF-Kb will take up the probe from the culture medium. In the intracellular reducing environment, the disulfide linkage should be cleaved, releasing the probe. After the cells are loaded with the labeled probe, excess extracellular probe can be removed by pelleting the cells, e.g., in a centrifuge, and re-suspending the pellet in a buffered cell medium, i.e., Hank's Balanced Salt Solution, containing a density adjusting material, e.g., Optiprep (Nicomet) at 11% w/v. The cell medium should prevent the cells from settling in the reaction vessel, e.g., microfluidic channels. The cells would then be placed in a well of a microfluidic device designed to transport the cells along an analysis channel, and mix the cells with test compounds. The cells/test compound mixture would then be incubated for approximately 60 seconds as they move along the channel past a fluorescence polarization detector. The signals that would be obtained from the cells are then averaged over a selected time period for each test compound injection, e.g., 20–60 seconds. In operation, it would be expected that signal could be detected that would be indicative of the binding interaction in the cells, and those signals could be compared to appropriate positive and/or negative controls.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

---

---

What is claimed is:

1. A method of detecting intracellular binding interactions, comprising:
    providing a biological cell having at least a first component of a binding reaction disposed therein;
    contacting the cell with a second component of the binding reaction whereby the second component is internalized within the biological cell, the second component comprising a non-protein molecule, at least one of the first and second components having a fluorescent label associated therewith; and
    determining an amount of binding between the first and second components within the cell by measuring a level of polarized fluorescence emitted from within the biological cell.

2. The method of claim 1, wherein the second component comprises a binding fragment of a full length protein that is capable of binding the first component.

3. The method of claim 2, wherein the second component is between about 4 and about 50 residues in length.

4. The method of claim 2, wherein the second component is between about 4 and 100 residues in length.

5. The method of claim 2, wherein the second component comprises a molecular weight less than about 10 kD.

6. The method of claim 2, wherein the second component comprises a molecular weight less than about 5 kD.

7. The method of claim 1, wherein the second component is selected from a carbohydrate, a lipid, cAMP, cGMP and diacylglycerol.

8. The method of claim 1, wherein the first component comprises an intracellular nucleic acid binding protein and the second component comprises a nucleic acid probe.

9. The method of claim 8, wherein the nucleic acid probe is from about 5 to about 100 bases in length.

10. The method of claim 8, wherein the nucleic acid probe is from about 10 to about 50 bases in length.

11. The method of claim 8, wherein the first component comprises a DNA binding protein and the second component comprises a fluorescently labeled DNA probe.

12. The method of claim 11, wherein a level of affinity of the DNA binding protein and the DNA probe is increased or decreased upon activation of a cell signaling pathway.

13. The method of claim 12, wherein the cell signaling pathway is activated by binding of a ligand to a cellular receptor.

14. The method of claim 8, wherein the nucleic acid probe comprises a translocation finctionality.

15. The method of claim 14, wherein the translocation functionality comprises a translocating peptide.

16. The method of claim 15, wherein the translocating peptide comprises Antp-HD or a fragment thereof.

17. The method of claim 15, wherein the translocating peptide comprises a polypeptide that includes a sequence homologous to residues 48–60 of an HIV-1 tat protein (SEQ ID NO:1).

18. The method of claim 8, wherein the nucleic acid binding protein is a component of a cell signaling pathway, activation of the pathway activating or deactivating the nucleic acid binding protein.

19. The method of claim 1, wherein the cell is selected from a mammalian cell, bacterial cell, fungal cell, yeast cell, insect cell, and a plant cell.

20. The method of claim 19, wherein the cell is a mammalian cell that is selected from a CHO cell, a HEK-293 cell, a L-cell, a 3T3 cell, a COS cell, a THP-1 cell, a RBL-1 cell, a YB-1 cell, a Jurkat cell and a U937 cell.

21. The method of claim 1, wherein the determining step comprises:

directing a polarized excitation light at the cell;

measuring a level of polarized or depolarized fluorescence emitted from within the cell; and comparing a level of polarized or depolarized fluorescence emitted from within the cell to a control, to determine a level of the intracellular binding reaction that occurred in the cell.

22. The method of claim 1, wherein the cell is provided in a suspension of cells.

23. The method of claim 1, wherein the cell is disposed in a reaction vessel having a window for optically accessing the cell.

24. The method of claim 23, wherein the reaction vessel comprises a test tube.

25. The method of claim 23, wherein the reaction vessel comprises a cuvette.

26. The method of claim 23, wherein the reaction vessel comprises a well in a multiwell plate.

27. The method of claim 23, wherein the reaction vessel comprises at least a first fluidic channel.

28. The method of claim 27, wherein the first fluidic channel comprises at least a first microscale fluidic channel disposed within a body structure.

29. The method of claim 28, wherein the microscale fluidic channel comprises a first of at least two intersecting microscale channels disposed in the body structure.

30. The method of claim 1, further comprising:

exposing said cell to a test compound prior to the determining step; and comparing an amount of binding between the first and second components within the cell in the presence of the test compound to an amount of binding between the first and second components within the cell in the absence of the test compound, the comparing step occurring after the determining step.

31. The method of claim 30, wherein the exposing and comparing steps are separately repeated for a plurality of different test compounds.

32. A method of monitoring activation of a cell signaling pathway, comprising:

providing a cell which comprises a cell signaling pathway, wherein at least one step in the cell signaling pathway comprises an intracellular binding interaction between a nucleic acid and a nucleic acid binding protein;

contacting the cell with a first nucleic acid whereby the first nucleic acid is internalized within the cell, wherein the first nucleic acid comprises a fluorescent label and is capable of being bound by the nucleic acid binding protein; and monitoring a level of binding between the nucleic acid binding protein and the first nucleic acid by monitoring a level of depolarized fluorescence emitted from within the cell, the amount of depolarized fluorescence being indicative of a level of activation of the cell signaling pathway.

33. A method of screening for effectors of cellular function, comprising:

providing at least a first cell capable of at least one cellular function that is initiated by interaction of a nucleic acid sequence and a nucleic acid binding protein;

inserting a first nucleic acid having a fluorescent label associated therewith into the cell, wherein the first nucleic is capable of being bound by the nucleic acid binding protein;

exposing the cell to a test compound;

determining an amount of binding between the first and second components within the cell by measuring a level of polarized fluorescence emitted from within the biological cell; and comparing an amount of binding between the first and second components within the cell in the presence of the test compound to an amount of binding between the first and second components within the cell in the absence of the test compound.

* * * * *

UNITED STATES PATENT AND TRADEMARK OFFICE
CERTIFICATE OF CORRECTION

PATENT NO.    : 6,379,884 B2
DATED         : April 30, 2002
INVENTOR(S)   : Wada et al.

It is certified that error appears in the above-identified patent and that said Letters Patent is hereby corrected as shown below:

Column 17,
Line 25, please delete "finctionality" and insert -- functionality --.

Signed and Sealed this

Second Day of July, 2002

Attest:

JAMES E. ROGAN
*Attesting Officer*   *Director of the United States Patent and Trademark Office*

SEQUENCE LISTING

<160> NUMBER OF SEQ ID NOS: 1

<210> SEQ ID NO 1
<211> LENGTH: 15
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: cysacetamidomethyl

<400> SEQUENCE: 1

Xaa Gly Arg Lys Lys Arg Arg Gln Arg Arg Arg Pro Pro Gln Cys
1               5                   10                  15